United States Patent
Pryor

(10) Patent No.: US 11,668,668 B2
(45) Date of Patent: Jun. 6, 2023

(54) MECHANISM FOR THE REAL-TIME PREDICTION OF INCIPIENT FAILURE IN WORKING FLUIDS

(71) Applicant: Pryor Knowledge Systems, Inc., Bloomfield Hills, MI (US)

(72) Inventor: Roger W. Pryor, Bloomfield Hills, MI (US)

(73) Assignee: PRYOR KNOWLEDGE SYSTEMS, INC., Bloomfield Hills, MI (US)

( * ) Notice: Subject to any disclaimer, the term of this patent is extended or adjusted under 35 U.S.C. 154(b) by 256 days.

(21) Appl. No.: 17/063,079

(22) Filed: Oct. 5, 2020

(65) Prior Publication Data

US 2022/0107284 A1    Apr. 7, 2022

(51) Int. Cl.
*G01N 27/10* (2006.01)
*G01N 33/28* (2006.01)

(52) U.S. Cl.
CPC ......... *G01N 27/10* (2013.01); *G01N 33/2847* (2013.01); *G01N 33/2888* (2013.01)

(58) Field of Classification Search
CPC . G01N 27/10; G01N 33/2847; G01N 33/2888
See application file for complete search history.

(56) References Cited

U.S. PATENT DOCUMENTS

| | | | | |
|---|---|---|---|---|
| 6,028,433 | A * | 2/2000 | Cheiky-Zelina | G01N 27/026 324/672 |
| 6,861,851 | B2 * | 3/2005 | Lvovich | G01N 33/2888 324/553 |
| 7,259,575 | B2 * | 8/2007 | Lvovich | G01N 33/2888 324/698 |
| 7,541,004 | B2 * | 6/2009 | Niksa | G01N 27/126 324/698 |
| 10,274,445 | B2 * | 4/2019 | Diez Garcia | G01N 27/07 |
| 2004/0060344 | A1 * | 4/2004 | Kauffman | G01N 33/2847 73/53.01 |
| 2004/0075448 | A1 * | 4/2004 | Lvovich | G01N 33/2888 324/707 |
| 2009/0026090 | A1 * | 1/2009 | Danyluk | G01N 33/2888 205/775 |
| 2020/0003730 | A1 * | 1/2020 | Winecki | G01N 33/241 |

FOREIGN PATENT DOCUMENTS

WO    WO-2009015090 A1 *    1/2009    ............. G01N 27/02

OTHER PUBLICATIONS

"Frequency Domain Modeling of a Capacitor" COMSOL Software License Agreement 5.5, www.comsol.com/trademarks.

* cited by examiner

*Primary Examiner* — Jamel E Williams
(74) *Attorney, Agent, or Firm* — John A. Miller; Shumaker, Loop & Kendrick, LLP

(57) ABSTRACT

A system and method for determining whether a working fluid being used in a machine is near its failure point. The system includes an impedance/admittance sensor having a flow chamber through which the working fluid flows and a pair of spaced apart electrodes. A function generator generates frequency signals at certain frequencies over a range of frequencies and a sensor circuit receives the frequency signals and provides the frequency signals to the electrodes, where the conductance of the working fluid creates a measurement signal in the sensor circuit. A processor is responsive to the measurement signal and generates a relationship between the frequency signals and the measurement signal that is indicative of a contamination level of the working fluid.

16 Claims, 2 Drawing Sheets

MECHANISM FOR THE REAL-TIME PREDICTION OF INCIPIENT FAILURE IN WORKING FLUIDS

BACKGROUND

Field

This disclosure relates generally to a system and method for determining the integrity of a working fluid as it is being used in a machine and, more particularly, to a system and method for determining whether a working fluid being used in a machine is near its failure point by monitoring the admittance of the working fluid.

Discussion of the Related Art

Most machines and mechanical systems, such as factory machines, vehicles, planes, ships, weapons, submarines, etc., operate using working fluids, such as lubricants, pressure transfer agents, engine oil, transmission fluid, hydraulic fluid, coolants, etc., that are employed as lubricants, coolants and pressure transfer agents. Typically, as the machine is being used, its working fluids will eventually be unable to properly perform their designed function and will fail. This failure occurs after some period of operational time in response to both mechanical and thermal cycling of the fluid and the fluid becoming contaminated as a result of the introduction of metal particles, carbon particles, water, other fluids, dirt, etc. into the working fluid. Failure of the working fluid could cause a catastrophic failure of the machine.

To ensure that machines and mechanical systems and their components are not damaged by contaminated working fluid, the fluid is periodically removed and replaced with new fluid before any catastrophic event in the machine can occur. Some working fluids, such as synthetic oils, typically used for expensive machinery are expensive themselves and for some machines need to be replaced often, which can be both costly and time consuming. Therefore, in order to get as much life out of the working fluid as possible without the risk of fluid failure, for certain applications the used fluid may be subjected to a complicated analysis process to ensure that the fluid replacement period is proper for the machine and that the machine is not in need of immediate repair as a result of metal shavings and the like in the fluid. However, this procedure is also costly, time consuming and does not always work in a timely manner to prevent machine failure. A better procedure would be to analyze the integrity of the working fluid in real-time to determine impending fluid failure while it is being used in the machine.

SUMMARY

The following discussion discloses and describes a system and method for determining whether a working fluid being used in a machine is near its failure point. The system includes an impedance/admittance sensor having a flow chamber through which the working fluid flows and a pair of spaced apart electrodes. A function generator generates frequency signals at certain frequencies over a range of frequencies and a sensor circuit receives the frequency signals and provides the frequency signals to the electrodes, where the conductance of the working fluid creates a measurement signal in the sensor circuit. A processor is responsive to the measurement signal that generates a relationship between the frequency signals and the measurement signal that is indicative of a contamination level of the working fluid and provides a warning to the operator.

Additional features of the disclosure will become apparent from the following description and appended claims, taken in conjunction with the accompanying drawings.

DETAILED DESCRIPTION OF THE EMBODIMENTS

The following discussion of the embodiments of the disclosure directed to a system and method for determining the integrity of a working fluid being used in a machine by monitoring the impedance/admittance of the fluid is merely exemplary in nature, and is in no way intended to limit the disclosure or its applications or uses.

This disclosure proposes a technique for determining whether a working fluid being used in a machine is nearing its failure point by providing a real-time analysis of the differential electrical impedance/admittance of the working fluid. More particularly, the electrical impedance/admittance of the working fluid changes in the frequency domain as a function of the shift in the electrical conductivity and/or the relative permittivity of the fluid that occurs because of the contamination level. The real-time prediction of the incipient failure of the working fluid will allow the fluid to be used in a particular machine for an optimum period of time, where the prediction of fluid failure is both machine and fluid independent. The real-time prediction of the failure of the working fluid also inherently compensates for the variability of both new fluids and the variability of the incipient fluid failure mechanisms from machine to machine. Once the incipient failure of the fluid is detected, the contaminated working fluid can be removed and replaced with new working fluid before the machine is damaged.

The impedance/admittance of a working fluid is determined by the combined properties of the basic fluid and those of the added contaminants. When the impedance/admittance of the fluid is measured as a function of the applied frequency, the added contaminants in the fluid cause the curve of the frequency/impedance relationship to be different from the curve of the original, pure working fluid. The extent of the difference between the two measured curves can be used to predict the proximity of incipient failure of the fluid. In other words, by knowing the time when the new fluid is put into the machine and the current contamination state of the working fluid, the time to the failure of the fluid can be accurately estimated, where that time can be adjusted if the contamination rate of the fluid increases.

The analysis of the characteristic electrical properties of the working fluid and how its properties change as the fluid ages can be found in the following equations.

$$Y = 1/Z,$$

$$Z = R + jX,$$

where Y is admittance, measured in siemens, Z is impedance, measured in ohms, R is resistance (real part), measured in ohms, X is reactance (imaginary part), measured in ohms, and j is the square root of minus one (−1).

Figure 1:
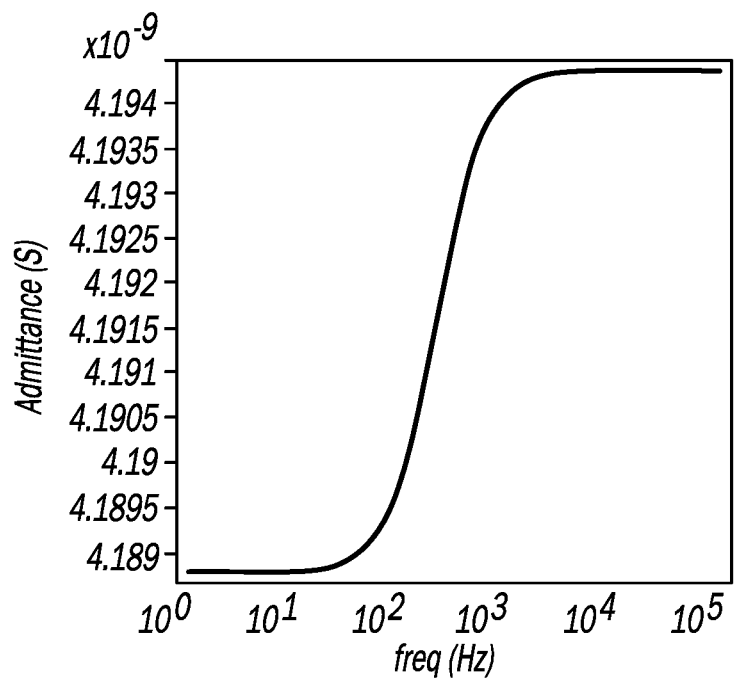
FIG. 1 is a graph of the logarithm of the frequency on the horizontal axis and the admittance on the vertical axis showing the relationship between the logarithm of the frequency and the admittance for pure engine oil.
Figure 2:
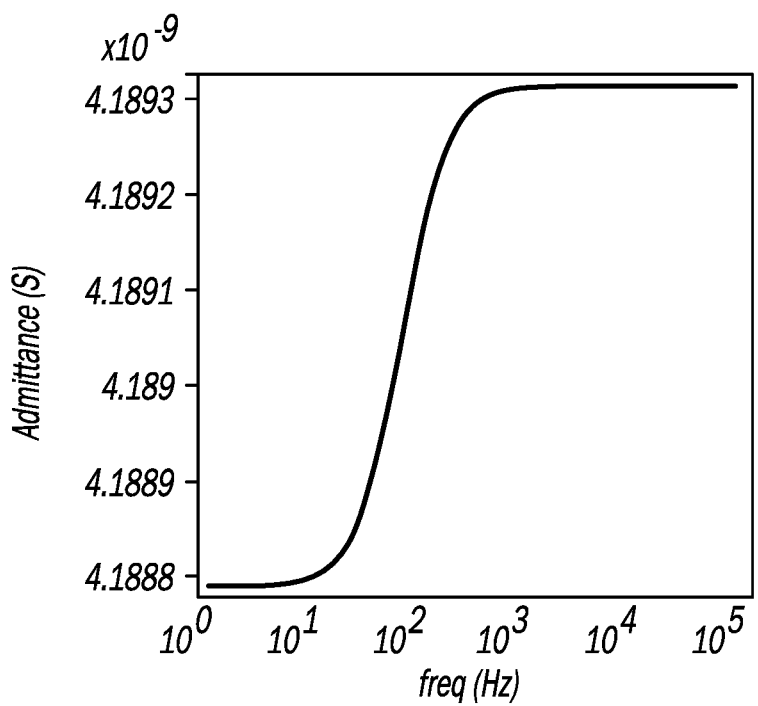
FIG. 2 is a graph of the logarithm of the frequency on the horizontal axis and the admittance on the vertical axis showing the relationship between the logarithm of the frequency and the admittance for engine oil contaminated with a small amount of water.
Figure 3:
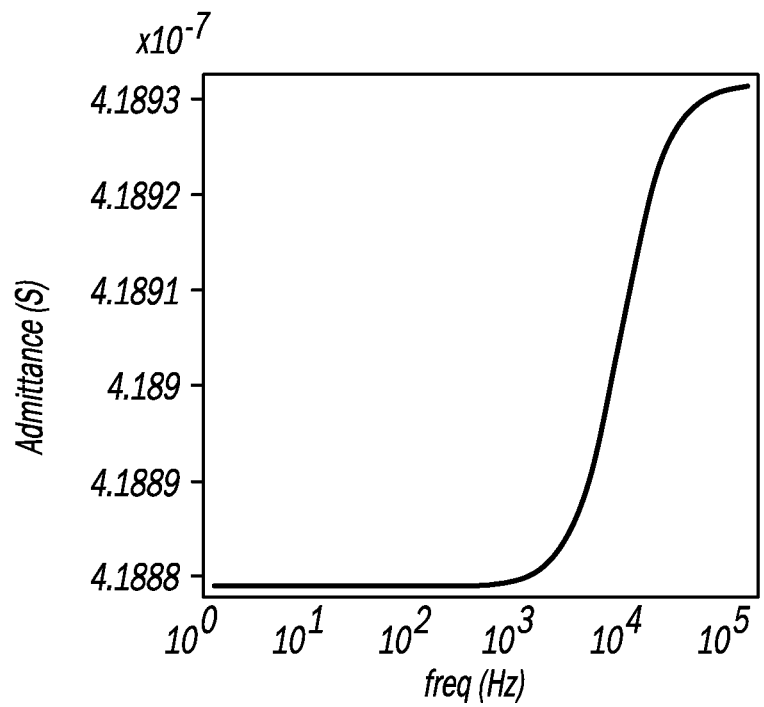
FIG. 3 is a graph of the logarithm of the frequency on the horizontal axis and the admittance on the vertical axis showing the relationship between the logarithm of the frequency and the admittance for engine oil contaminated with a small amount of water and metal particles.

The impedance/frequency relationship used in the comparison discussed above is illustrated by the graphs in FIGS. 1, 2 and 3. Particularly, FIG. 1 is a graph of the logarithm of the frequency on the horizontal axis and the admittance on the vertical axis showing the relationship between the logarithm of the frequency and the admittance for pure engine oil, FIG. 2 is a graph of the logarithm of the frequency on the horizontal axis and the admittance on the vertical axis showing the relationship between the logarithm of the frequency and the admittance for engine oil contaminated with a small amount of water, and FIG. 3 is a graph of the logarithm of the frequency on the horizontal axis and the admittance on the vertical axis showing the relationship between the logarithm of the frequency and the admittance for engine oil contaminated with a small amount of water and metal particles. As is apparent, the graphs in FIGS. 1, 2 and 3 are different and once it is known what the relationship between frequency and admittance is for a working fluid that is contaminated to an extent which could cause fluid failure, that knowledge can be used to determine when the fluid will likely fail.

Various designs of sensors and electrical configurations can be employed to obtain a relationship between an applied frequency to a working fluid and the measured impedance/admittance of the working fluid in response to the frequency. One suitable non-limiting example is discussed below, but as will be appreciated by those skilled in the art, other designs and configurations may be equally applicable.

Figure 4:
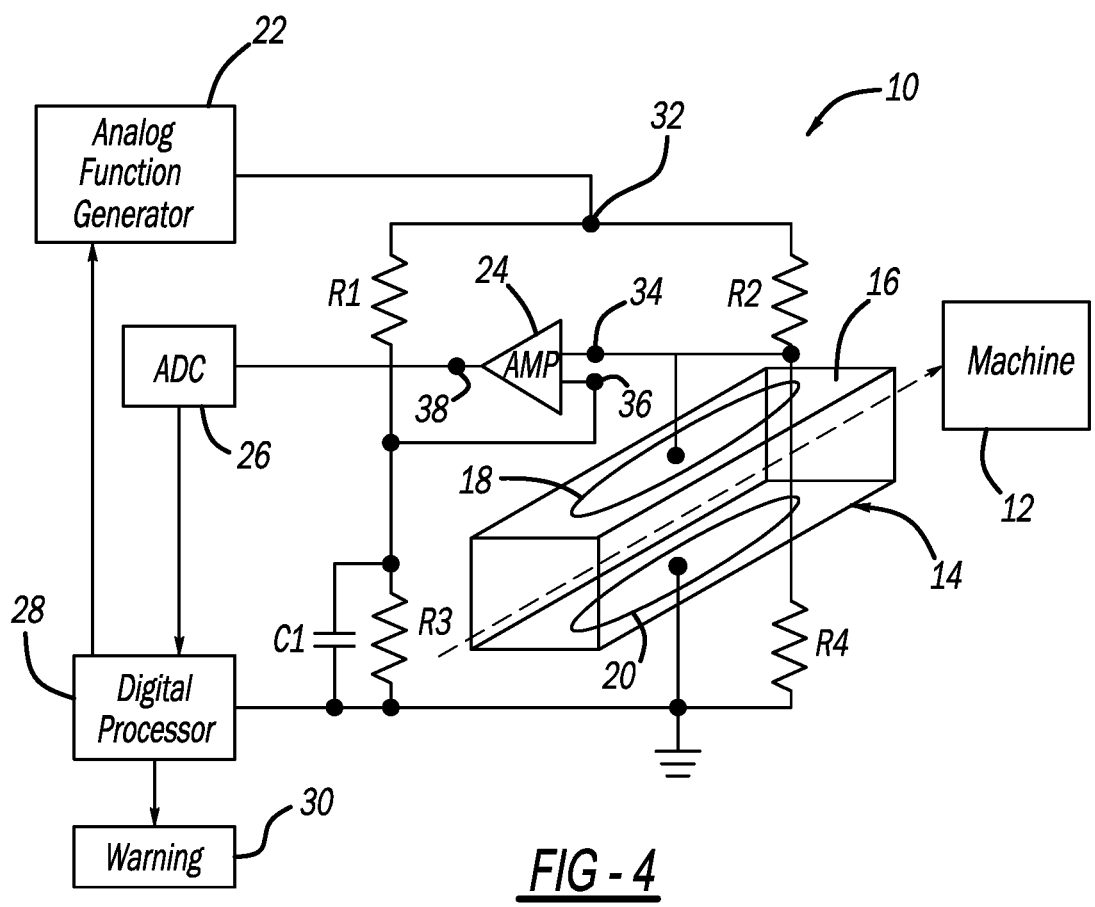
FIG. 4 is a schematic diagram of an impedance-admittance sensor system that determines the impedance/admittance of a working fluid as it is being used in a machine and provides a warning to the operator.

FIG. 4 is a schematic diagram of an impedance/admittance sensor system 10 that determines the impedance/admittance of a working fluid as it is being used in a machine 12, where the machine 12 is intended to represent any machine, such as factory machines, vehicles, planes, ships, weapons, submarines, etc., that uses a working fluid of any type, such as engine oil, transmission fluid, hydraulic fluid, coolants, etc. The system 10 includes an impedance/admittance sensor 14 having a chamber 16 and spaced apart electrodes 18 and 20 where the working fluid flows through the chamber 16 between the electrodes 18 and 20 as the machine 12 operates. An analog function generator 22 generates an analog function signal at selected and periodic frequencies over a range of frequencies, such as every 100 Hz from 1 Hz to 1 MHz generally as a pulse.

The function signal is applied to a node 32 at the top of a bridge detection assembly including resistors R1, R2, R3 and R4, capacitor C1 and the sensor 14. The detection bridge assembly includes a reference branch having the resistors R1 and R3 and the capacitor C1 and a detection branch having the resistors R2 and R4 and the sensor 14. The values of the resistors R1 and R3 and the capacitor C1 are chosen and adjusted to provide a balanced input to an analog differential amplifier 24 when pure working fluid is flowing through the sensor 14. The differential function signals at the junctions of R1-R3 and R2-R4 are applied to input nodes 36 and 34 of the amplifier 24, respectively. The amplified voltage difference between the inputs of the differential amplifier 24 at output node 38 of the amplifier 24 is provided to an analog-to-digital converter (ADC) 26 that converts the signal to a digital signal that is processed by a digital processor 28, which converts the voltage difference to an impedance and/or admittance using the equations above.

As the function generator 22 sweeps the frequency across the desired frequency range, the processor 28 generates frequency/admittance curves at a predetermined rate and stores at least some of those curves. As the working fluid becomes more contaminated during continued use and the conductance between the electrodes 18 and 20 changes in response thereto, the voltage at the input to the differential amplifier 24 changes, and thus the frequency/admittance curve also changes. When a new curve is generated, the processor 28 will compare that curve to one or more previous curves to determine if the contamination level of the working fluid is nearing its failure point. If that occurs, the processor 28 can send an alert to a warning device 30 to have the working fluid replaced.

The foregoing discussion discloses and describes merely exemplary embodiments of the present disclosure. One skilled in the art will readily recognize from such discussion and from the accompanying drawings and claims that various changes, modifications and variations can be made therein without departing from the spirit and scope of the disclosure as defined in the following claims.

What is claimed is:

1. A system for determining the integrity of a working fluid as it is being used in a machine, said system comprising:
   a sensor including a flow chamber and a pair of spaced apart electrodes, said working fluid being operable to flow through the chamber between the electrodes;
   a function generator generating a function signal over a range of frequencies;
   a sensor circuit responsive to the function signal and providing the function signal to the electrodes, wherein the conductance of the working fluid creates a measurement signal in the sensor circuit, and wherein the sensor circuit includes a differential amplifier having two input terminals responsive to the function signals, where one terminal is electrically coupled to one of the electrodes and another terminal is connected to a reference standard and an output of the differential amplifier, wherein the differential output of the amplifier is the measurement signal at the time of measurement for the applied function signal from the function generator; and
   a processor responsive to the measurement signal and generating a relationship between the function signals and the measurement signal that is indicative of a contamination level of the working fluid.

2. The system according to claim 1 wherein the processor compares the relationship between the function signals and the measurement signal with previously generated relationships between the function signals and the measurement signal to determine the contamination level of the working fluid.

3. The system according to claim 2 wherein the processor determines when the working fluid may fail based on the comparison.

4. The system according to claim 1 wherein the function generator generates the function signals at periodic frequencies in the range of 1 Hz to 1 MHz.

5. The system according to claim 1 wherein the processor converts the measurement signal to an impedance or an admittance and generates a relationship between the function signals and the impedance or admittance.

6. The system according to claim 1 wherein the working fluid is selected from the group consisting of lubricants, pressure transfer agents, engine oil, transmission fluid, hydraulic fluid and coolants.

7. An impedance/admittance measurement system for measuring the impedance/admittance of a working fluid as it is being used in a machine, said system comprising:
an impedance/admittance sensor including a flow chamber and a pair of spaced apart electrodes, said working fluid being operable to flow through the chamber between the electrodes;
a function generator generating a periodic frequency signal over a range of frequencies;
a sensor circuit responsive to the frequency signal and providing the frequency signal to the electrodes, wherein the conductance of the working fluid creates a measurement signal in the sensor circuit, wherein the sensor circuit includes a differential amplifier having two input terminals responsive to the frequency signals, where one terminal is electrically coupled to one of the electrodes and another terminal is connected to a reference standard and an output of the differential amplifier, wherein the differential output of the amplifier is the measurement signal at the time of measurement for the applied frequency signal from the function generator; and
a processor responsive to the measurement signal and converting the measurement signal to an impedance or an admittance, said processor generating a relationship between the frequency signals and the impedance or admittance and comparing the relationship between the frequency signals and the impedance or admittance with previously generated relationships between the frequency signals and the impedance or admittance to determine the contamination level of the working fluid.

8. The system according to claim 7 wherein the processor determines when the working fluid may fail based on the comparison.

9. The system according to claim 7 wherein the function generator generates the frequency signals at periodic frequencies in the range of 1 Hz to 1 MHz.

10. The system according to claim 7 wherein the working fluid is selected from the group consisting of lubricants, pressure transfer agents, engine oil, transmission fluid, hydraulic fluid and coolants.

11. A method for determining the integrity of a working fluid as it is flowing through a machine, said method comprising:
flowing the working fluid between a pair of electrodes;
applying a frequency signal to the electrodes;
generating a measurement signal from the electrodes, wherein generating a measurement signal includes providing an analog differential amplifier having two input terminals responsive to the frequency signal, wherein one terminal is coupled to one of the electrodes and another terminal is connected to a reference standard and an output of the analog differential amplifier, and wherein the output of the differential amplifier is electrically coupled to an analog-to-digital converter to convert the output to a digital value of the measurement signal;
generating a relationship between the frequency signal and the measurement signal; and
comparing the relationship to previously generated relationships between the frequency signal and the measurement signal.

12. The method according to claim 11 wherein applying a frequency signal to the electrodes includes applying a frequency signal at periodic frequencies over a range of frequencies.

13. The method according to claim 12 wherein the frequency signals are every 100 Hz from 1 Hz to 1 MHz.

14. The method according to claim 11 wherein generating a relationship between the frequency signal and the measurement signal includes converting the measurement signal to an impedance or an admittance and generating a relationship between the frequency signal and the impedance or admittance.

15. The method according to claim 11 wherein the working fluid is selected from the group consisting of lubricants, pressure transfer agents, engine oil, transmission fluid, hydraulic fluid and coolants.

16. The method according to claim 11 further comprising determining when the working fluid may fail based on the comparison and initiating a warning signal of incipient failure of the working fluid.

* * * * *